(12) United States Patent
Bordeaux

(10) Patent No.: US 10,035,635 B2
(45) Date of Patent: Jul. 31, 2018

(54) PACKAGING DEVICE

(71) Applicant: L'OREAL, Paris (FR)

(72) Inventor: Dominique Bordeaux, Soisy sur Seine (FR)

(73) Assignee: L'OREAL, Paris (FR)

(*) Notice: Subject to any disclaimer, the term of this patent is extended or adjusted under 35 U.S.C. 154(b) by 36 days.

(21) Appl. No.: 14/902,694

(22) PCT Filed: Jul. 1, 2014

(86) PCT No.: PCT/IB2014/062769
§ 371 (c)(1),
(2) Date: Jan. 4, 2016

(87) PCT Pub. No.: WO2015/001486
PCT Pub. Date: Jan. 8, 2015

(65) Prior Publication Data
US 2016/0167856 A1    Jun. 16, 2016

(30) Foreign Application Priority Data

Jul. 2, 2013 (FR) ..................... 13 56467

(51) Int. Cl.
*B65D 75/20* (2006.01)
*B65D 75/30* (2006.01)
*B65D 75/58* (2006.01)
*B65D 83/00* (2006.01)
*B65B 63/04* (2006.01)
(Continued)

(52) U.S. Cl.
CPC ............. *B65D 75/20* (2013.01); *B65B 63/04* (2013.01); *B65D 75/30* (2013.01); *B65D 75/58* (2013.01); *B65D 83/00* (2013.01); *A45D 44/002* (2013.01); *A61K 8/0212* (2013.01); *B65D 2313/10* (2013.01)

(58) Field of Classification Search
CPC ...... B65D 75/20; B65D 75/30; B65D 75/305; B65D 75/5855; B65D 75/26; B65D 75/322; A45D 44/002; A61K 8/0212
USPC ........ 132/319; 206/210, 438, 440, 441, 812; 428/74
See application file for complete search history.

(56) References Cited

U.S. PATENT DOCUMENTS 3,485,349 A   12/1969  Chaney, Jr.
5,046,608 A    9/1991  Laipply
(Continued)

FOREIGN PATENT DOCUMENTS

CA    2 313 216 A1    1/2001
WO    2012077563 A1   6/2012

OTHER PUBLICATIONS

Oct. 10, 2014 Search Report issued in International Patent Application No. PCT/IB2014/062769.
(Continued)

*Primary Examiner* — Anthony Stashick
*Assistant Examiner* — Mollie Impink
(74) *Attorney, Agent, or Firm* — Oliff PLC

(57) ABSTRACT

The present invention relates to a device (1) for packaging a product, comprising:—a container (2) having joined front and rear walls,—an article (3) packaged in a folded state inside the container (2), this article (3) bearing said product, having at least two sections separated by at least one fold line (4), at least one of these two sections being attached to one of the front and rear walls by at least one weld zone (5).

13 Claims, 2 Drawing Sheets

Figure 10:
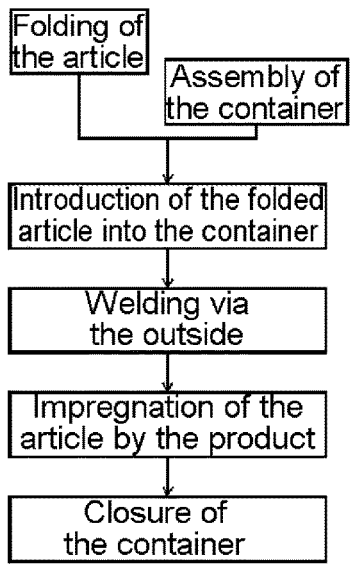

(51) Int. Cl.
A61K 8/02 (2006.01)
A45D 44/00 (2006.01)

(56) References Cited

U.S. PATENT DOCUMENTS 5,487,932 A * 1/1996 Dunshee ............ B65D 75/5855
  15/104.93
2003/0153091 A1 8/2003 Willard et al.
2009/0255554 A1* 10/2009 Omoto ................ A45D 44/002
  132/319

OTHER PUBLICATIONS

Oct. 10, 2014 Written Opinion issued in International Patent Application No. PCT/IB2014/062769.

* cited by examiner

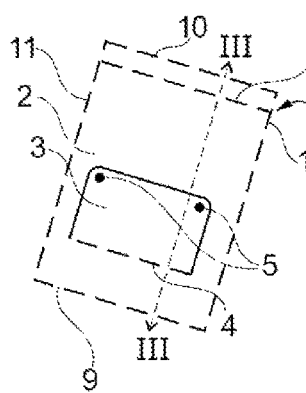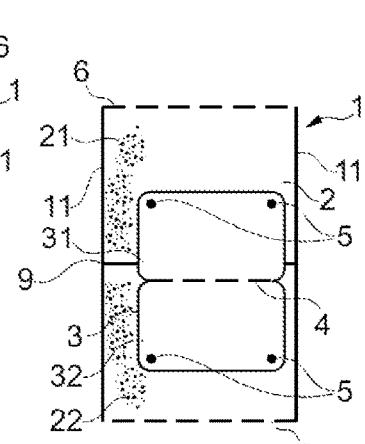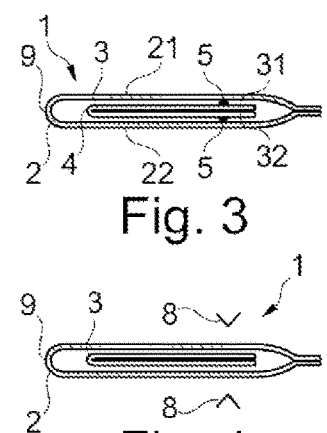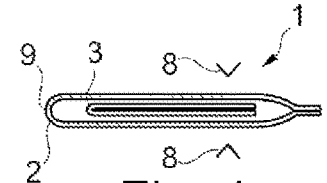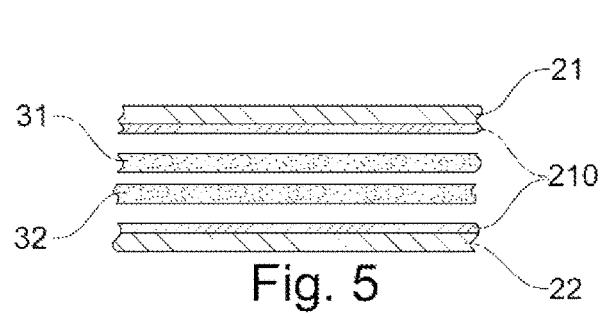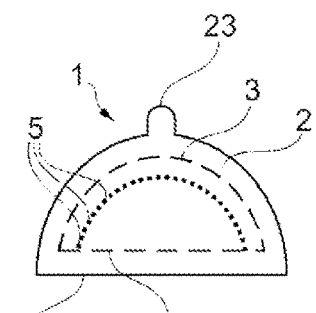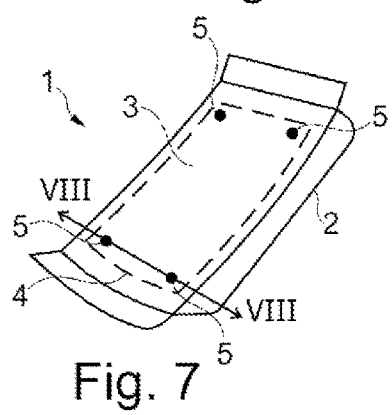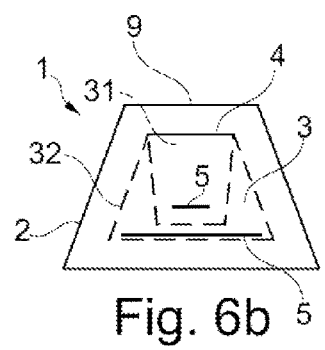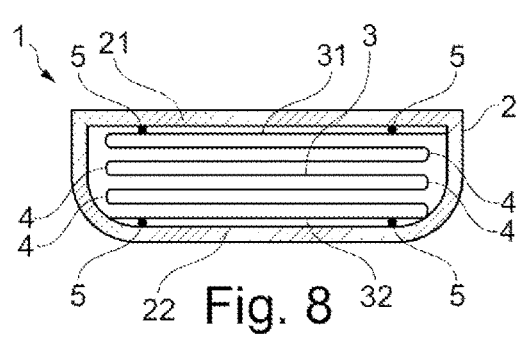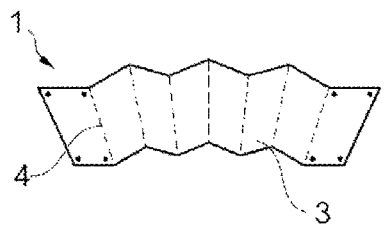

PACKAGING DEVICE

The present invention relates to a device for packaging a product, comprising a container having joined front and rear walls and an article packaged inside the container.

European patent application EP 1 095 589 discloses a hermetically sealed pouch containing a mask impregnated with a cosmetic composition, the mask being in its opened out form in the pouch.

French patent application FR 2 971 933 describes a cosmetic mask comprising a sheet of a stretchable nonwoven material. Markers may be produced by local melting of the material of the mask, in order to indicate to the user how to stretch the latter.

International application WO 2012/077563 discloses a package structure for an article for external application to the body. The article is sandwiched between a base film and a cover film. The assembly thus formed is folded on itself and welded over 3 sides so as to form a sachet with the cover film on the inside.

International application WO 2011/064901 discloses an article impregnated with cosmetic product that is folded and sandwiched between upper and lower sheets. The upper sheet can be partially detached from the lower sheet to facilitate the removal of the article.

United States patent application US 2010/0155284 describes a container that has a cut along which the container can be broken or folded, thus giving access to its contents.

International application WO 2008/075234 discloses a device comprising a substrate bearing a cosmetic composition and a support layer attached to the substrate. This support layer makes it possible to avoid direct contact with the substrate during application and it is detached from the substrate after positioning the latter on the appropriate part of the body.

French patent application FR 2 870 698 and Japanese patent application JP 2000-287751 describe masks for the face, which are folded in a manner that facilitates unfolding during use.

U.S. Pat. No. 5,046,608 discloses a fluid storage and application device comprising a pad disposed inside a cavity formed by a sheet-like impermeable material and adhered thereto.

U.S. Pat. No. 3,485,349 discloses a packet having an inner absorbent sheet adhesively attached an outer overwrap, the sheet being attached to a contiguous surface of said overwrap and comprising a line of weakness enabling the removal of the sheet from the overwrap.

Canadian patent application CA 2 313 216 describes a device comprising an outer packing material and an inner layer made from an absorbent material, this device being manufactured by applying the packing material against a rotating drum then by covering it with the inner layer.

When the article is a nonwoven in the impregnated state, folded and compacted inside the container, the impregnation tends to soften the nonwoven and weaken it. It increases the adhesion of the various sections of the article resulting from folding them and considerably affects the ease of unfolding of the article, thus increases the difficulty of the use thereof.

There is a need to further improve the devices for packaging an article bearing a product placed between the joined front and rear walls of a container, in order to facilitate the handling of the article during and after the opening of the container.

The invention aims to meet this need and it achieves this by virtue of a device for packaging a product, comprising:
  a container having joined front and rear walls,
  an article packaged in a folded state inside the container, this article bearing said product, having at least two sections separated by at least one fold line, at least one of these two sections being attached to one of the front and rear walls by at least one weld zone.

The fact that the article remains firmly attached by at least one section of one of the front and rear walls after opening of the container may facilitate the gripping of the article in order to unfold it, especially when the two sections have unequal dimensions and when the unwelded section juts out for example beyond the one that is welded.

Preferably, the two sections are respectively attached to the front and rear walls by weld zones, so that on opening the container the separation of the front and rear walls automatically leads to the unfolding of the article at least about said fold line, it being possible for the article to be separated from the walls via a pulling force exerted on the weld zones.

Owing to the invention, in particular in the case where the two sections are respectively attached to the front and rear walls, the opening of the container is accompanied by an at least partial unfolding of the article about the fold line, and the article is thus easier for the user to grasp properly. Furthermore, the invention makes it possible to avoid having to place the article on another surface in order to unfold it before the use thereof, which avoids possible soiling, caused by the impregnated composition or found on the support on which the article is placed, and improves the comfort of use and hygiene.

There may be only one fold line, the sections being of symmetrical shape or not with respect to the fold line, and the article may be folded up on the side of an opening of the container.

The expression "cosmetic product" is understood to mean a product as defined in Article 2 of Regulation No. 1223/2009 of the European Parliament and of the Council of 30 Nov. 2009.

The product may be in the form of a fluid composition, and the article may be impregnated with said product.

The article is preferably attached to the wall or walls of the container from the outside of the container. The weld zone(s) may be spot weld(s). For example, the device comprises two weld spots on each wall of the container. The weld spots may be located close to corners/free ends of each section of the article.

The article may comprise a sheet of a nonwoven material. The article may comprise a hot-melt material, in particular fibres of a hot-melt material. The front and rear walls of the container may also have, on their inner face, a layer of a hot-melt material.

The article may be detached from the wall(s) of the container by a pulling force exerted by the user. This pulling force may lead to rupture of the material of the weld zone itself and/or a local tearing of the material of the article, especially when the article is fibrous. In this case, fibres that ensure the joining of the article to the wall of the container may for example remain attached to the weld zone and be separated from the rest of the article. Optionally, the article may tear slightly at the welded zone and cause a small hole which is not detrimental to the properties of the impregnated article.

Another subject of the invention is a process for manufacturing a device according to the invention, the article being folded on itself about at least one fold line inside the container and having at least two sections separated by said fold line, in which process:

at least one of the sections of the article is attached to one of the front and rear walls of the container by at least one weld zone, and preferably the two sections of the article are respectively attached to the front and rear walls of the container by weld zones.

Preferably, the weld or welds are created from the outside of the container.

The impregnation of the article and the closure of the container may be carried out before or after attaching the article to said walls. As a variant, the article may be pre-impregnated before it is introduced inside the container. In a further variant, the section or sections of the article are attached to at least one of the walls of the container before the formation of the latter, in particular before joining the front and rear walls together.

Article

The article may be made from any material suitable for attaching it to the front and/or rear walls of the container.

In one preferred exemplary embodiment of the invention, it is the wall of the container that comprises a hot-melt material that makes it possible to ensure the attachment between the article and the wall of the container by local melting of material. As a variant, both the article and the wall of the container comprise one or more hot-melt materials that make it possible to ensure this attachment by local melting. As a further variant, only the article comprises a hot-melt material that enables the attachment by local melting.

When the container comprises a hot-melt material, the article advantageously has a porous, in particular fibrous, substrate facilitating bonding with the molten material of the wall of the container during the welding operation.

The article may be dry or, preferably, be impregnated with a liquid, pasty, powdery, etc. composition.

The capacity of the article to absorb the product may be linked to the use, for producing this article, at least partially, of a sheet of a porous, in particular fibrous, substrate, preferably a nonwoven or a paper. The nonwoven may be of any type, as specified further on.

The faces of the article may have any surface condition, and in particular be completely or partially embossed. They may be mechanically or chemically functionalized. Each face may have properties different from those of the other face.

The article may be single-layered or have a multilayer structure. The article may have several layers that can be separated from one another, where appropriate, as disclosed in application FR 1 260 840 filed on 14 Nov. 2012 by the proprietor.

The article may have only a single fold line, which is that defined above or, as a variant, at least one other fold line. In this case, the folding may be repeated several times on the same article and the invention makes it possible to partially unfold the article on opening the container, so that the user then has only one or more other unfolding steps to carry out. The availability of the article is nevertheless simplified with respect to the situation where the article is not firmly attached to the walls of the container.

The article may have, in the unfolded state, a contour of any shape, in particular polygonal or not, circular or oval. The article may in particular have a rectangular or more complex shape, adapted to a part of the body or face, for example a mask shape, the article having one or more cut-outs, for example for the eyes, nose and/or mouth.

The folding of the article may consist in folding the article on itself about a single fold line, symmetrically, the two sections positioned on either side of this line then being superposed exactly. As a variant, the folding may consist in folding the article about a fold line that does not lie in a median plane of symmetry of the article once the latter is unfolded. Thus, the sections thus positioned on either side of the fold line may not be superposed exactly, and one of the sections may for example jut out beyond the contour of the other section.

When the article comprises, in the packaged state, more than one fold line, the fold lines are for example parallel or perpendicular to one another.

Nonwoven

Within the meaning of the present invention, the term "nonwoven" denotes a substrate comprising fibres arranged in a disordered manner in a structure in the form of a sheet and that are neither woven nor knitted. The fibres of the nonwoven are generally bonded together, either under the effect of a mechanical action (for example needle punching, air jet, water jet, etc.), or under the effect of a thermal action, or by addition of a binder.

A nonwoven is in particular defined by the standard ISO 9092 as a web or sheet of directionally or randomly oriented fibres, bonded by friction and/or cohesion and/or adhesion, excluding paper and products which are woven, knitted, tufted or stitch-bonded incorporating binding yarns or filaments.

The nonwoven may be constituted of one or more consolidated webs of fibres.

The web(s) constituting the nonwoven may be of various compositions.

Fibres

The fibres of the nonwoven may be of various natures, in particular natural, modified natural, synthetic or artificial natures, alone or as a mixture in any proportions.

The non-woven preferably contains hot-melt fibres.

The hot-melt fibres are for example polyolefin fibres, such as polyethylene (PE), polypropylene (PP) or polyethylene terephthalate (PET) fibres or acrylic fibres such as polymethyl methacrylate (PMMA) fibres, polyurethane fibres or fibres of the following thermoplastics: polyvinyl chloride (PVC), styrene polymers (for example polystyrene PS, expandable polystyrene EPS, acrylonitrile-butadiene-styrene terpolymer ABS, styrene-acrylonitrile copolymer SAN, styrene-butadiene copolymer SB), polyamides (PA), polycarbonates (PC), saturated polyesters (for example polyethylene terephthalate glycol PETG, polybutylene terephthalate glycol PBTG), polyacetals (for example polyoxymethylene POM, trioxane-ethylene oxide copolymer), polyvinyl alcohol (PVA), or else fluoropolymers (for example polytetrafluoroethylene PTFE, polyvinylidene fluoride PVDF, polychlorotrifluoroethylene PCTFE).

The other optional fibres constituting the nonwoven are for example synthetic fibres derived from petroleum derivatives, natural fibres derived from plants or animals, and/or modified natural fibres, derived for example from treatment or regeneration processes in order to form fibres.

Welding

Preferably, the article is attached to the wall(s) without a cold-contact pressure-sensitive adhesive substance, such as a glue.

The article is attached to the walls of the container by welding.

The term "welding" should be understood to mean an attachment by melting of at least one material, locally. The melting may be carried out with, in particular, an ultrasonic welding process or a process of thermal welding by conduction or convection, and more generally by any process that makes it possible to generate complete or partial melting of the hot-melt compound(s) of the article and/or of its container, optionally with the presence of a hot-melt adhesive on the article and/or its container.

Preferably, the weld(s) of the article on the front and/or rear walls are created from the outside of the container, while these walls are already at least partially joined together.

During the welding operation, a pressing member may press against one wall of the container, and an input of thermal energy, for example via ultrasounds or via conduction or convection, is provided locally, at or in the vicinity of the zone compressed by the pressing member.

The compression makes it possible to improve the quality of the contact between the wall of the container and the article and to thus promote the bonding of the materials thereof. The compression may also, where appropriate, drive out the product present in liquid form between the article and the wall of the container to be attached to the article, capable of interfering with the weld.

The two walls of the container may be attached simultaneously to the article or as a variant firstly one wall of the container may be attached to the article then the opposite wall may be attached to the article. The welding operation is controlled so that the attachment of one wall of the container to the article does not weld the two front and rear walls together through the article nor overly impede the subsequent removal of the article at the time of use.

Preferably, the welding remains localized at zones of sufficiently small area so that the user can easily separate the article from the walls of the open container with a moderate pulling force. The welding is thus, preferably, spot welding and limited to a few anchorage points, for example two per wall of the container. The surface of the article attached by welding to the opposite wall of the container may have an area of less than or equal to 1 cm$^2$ per section of the article, preferably being between 0.1 mm$^2$ and 10 mm$^2$.

The separation of the article from the walls of the container may advantageously be carried out without adding a solvent after opening of the container, which would act on the weld(s) of the article and walls of the container in order to reduce the cohesion thereof.

Container

The container may have any shape suitable for packaging of the article in the folded state inside it.

Preferably, the container is produced so as to enable easy opening, in particular by separating the front and rear walls starting from one corner or one edge thereof.

The packaging may be in the form of a sachet or case.

Presentation in sachet form is favoured since it allows manufacture at a lower cost, compatible with a large-scale distribution of the device.

In the case in particular where the container is in the form of a sachet, the joined front and rear walls may be joined by welding with possibility of opening the container via a pulling force exerted on the two walls starting from one corner or one end of the sachet and/or from a tear initiation.

For this purpose, the container may have a gripping zone that enables the user to grasp the two front and rear walls before exerting the pulling force necessary for the separation thereof.

The container may be produced from two initially separate sheets that are joined to one another in order to constitute the front and rear walls or from one sheet which is folded on itself at one end in order to constitute said front and rear walls. The container may optionally have more than two faces, which is the case for example for a sachet with a flat bottom and two gussets on either side.

The material of the container may have a single-layer or multilayer structure. A multilayer structure is preferred since it facilitates the creation of a barrier function to oxygen and/or to light, useful for preservation of the product, for example achieved using a layer of metal, while preserving the ease of joining one sheet to another.

Preferably, the container has a thermoplastic material on its inner face intended to come into contact with the article, in order to facilitate the attachment via welding. This thermoplastic material is, for example, a polyolefin, in particular low-density or high-density polyethylene, low-density and high-density PP, etc.

The expression "thermoplastic material" denotes a material which softens under the effect of heat and which hardens on cooling, in a reversible manner.

The material constituting the front or rear wall of the container may comprise a multilayer structure with at least one layer of a metal, for example of aluminium. This material may also comprise a layer of a mechanically strong thermoplastic material, for example a non-olefinic material, such as a polyester, on which the layer of metal may be deposited.

The container may be sealed in a leaktight or non-leaktight manner. Leaktight sealing is preferred when the product is contained inside the latter in a fluid form, in particular liquid form, for example while impregnating the article.

When the product is dry, and when the article is intended to be moistened by a solvent, in particular water, during use, leaktight sealing of the container is not necessary, even if it is preferable.

The container may have, as a front view, before opening, a contour of any shape, in particular polygonal or not, circular or not, or oval. The container may optionally be pierced with cut-outs; in this case the front and rear walls are joined over their internal and external peripheries. The container is preferably opaque, but as a variant it is transparent or translucent.

Impregnation

The impregnation consists in making the product be absorbed by the article. The container may be filled with a product in order to impregnate the article.

The product contained inside the device may be of any type and in particular be for cosmetic, dermatological or other use.

Preferably, the product is for cosmetic or dermatological use, the article being intended to be applied to human keratin substances, especially to the skin and the hair.

The product is preferably in a liquid form inside the container, but as a variant this product may be in another form, in particular a dry or gelled form.

The product may comprise an aqueous or alcoholic solvent. The product may be a make-up, cleansing or care product.

Preferably, the article is porous and has a certain capacity for absorbing the product. Thus, the article may be impregnated, in particular to saturation, by the product when the latter is liquid. The impregnation of the article by the product may be carried out while the article is already in place inside the container and the latter is not yet completely sealed, the product being, for example, introduced into the container with the aid of a filling nozzle inserted into an opening of the container. As a variant, the article is pre-impregnated before being packaged between the front and rear walls of the container.

In the case where the container is filled with product before closure, it may be advantageous to attach the article to the walls of the container before the filling operation; this favours the article being held in place inside the container during filling, and may facilitate the latter.

In a further variant, the article bears a solid product and is packed dry in the container, and the user brings the latter extemporaneously into contact with a solvent, for example water, in order to solubilize the product present on the article.

Figure 11:
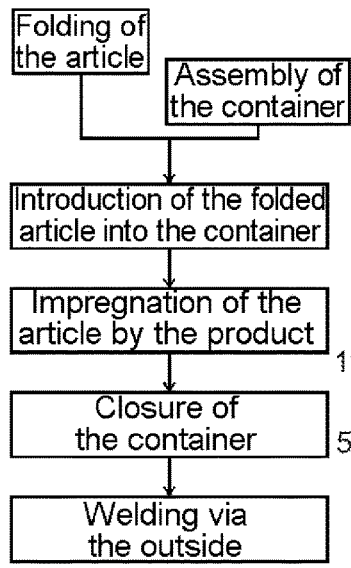
Figure 12:
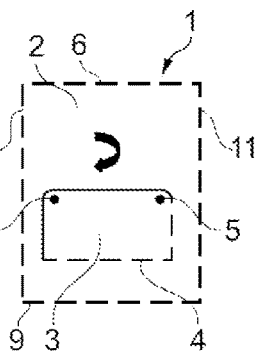

The invention may be better understood on reading the following detailed description of non-limiting illustrative embodiments thereof and on examining the appended drawings, in which:

FIG. 1 is a schematic front view of a packaging device according to one embodiment of the invention, the container not being open, FIG. 2 is a view of the container from FIG. 1 after opening, FIG. 3 is a longitudinal cross section along III-III in FIG. 1, FIG. 4 is a view similar to FIG. 3 before the welding of the front and rear walls of the container with the article, FIG. 5 represents, in cross section, the article and the front and rear walls before welding, FIGS. 6A and 6B are two front views of embodiment variants of devices according to the invention, FIG. 7 schematically represents, in perspective, an embodiment variant of a device according to the invention, FIG. 8 is a transverse cross section along VIII-VIII from FIG. 7, FIG. 9 represent the article contained in the device from FIGS. 7 and 8 after unfolding, FIGS. 10 and 11 are block diagrams illustrating various steps of the manufacturing process according to the invention, FIG. 12 illustrates the opening of the container from FIG. 1, and FIGS. 13A to 13F illustrate various steps of opening a device according to one embodiment variant of the invention.

The packaging device 1 according to the invention represented in FIGS. 1 to 3 and FIG. 12 comprises a container 2, in sachet form, and an article 3 packaged inside.

The container 2 comprises a front wall 21 and a rear wall 22 joined at their periphery over their four sides so as to define a leaktight inner volume containing the article 3.

In the example illustrated, the front wall 21 and rear wall 22 are made by folding one and the same flexible sheet about one side which defines the bottom 9 of the container 2. It is not outside the scope of the present invention when the front wall 21 and rear wall 22 are constituted of two independent sheets that are joined over their four sides in order to define the leaktight inner volume containing the article 3.

The opening of the container 2 at the edge 10 opposite the bottom 9 may be carried out by any means, for example by simple pulling force exerted on the front wall 21 and rear wall 22 so as to part them from one corner of the container 2, the separation then taking place along join lines 11 of the walls, for example.

As a variant, the opening of the container 2 may be carried out by exerting a pulling force at a location having a tear initiation, for example in the form of a small notch. As a further variant, the user may cut the container 2 with scissors along its upper part following a direction 6 parallel to the edge 10 of the container 2.

In accordance with the invention, the article 3 is present in the container 2 in the folded state, folded about at least one fold line 4 and the two sections 31, 32 of the article are respectively joined to the front wall 21 and rear wall 22 by weld spots 5.

Thus, when the container 2 is opened by separating the front wall 21 and rear wall 22, as illustrated in FIGS. 2 and 12, the article 3 is opened out at the same time about the fold line 4 in order to accompany the opening of the container 2. The article 3 is thus unfolded, ready for use, and rests on the walls 21, 22 of the container 2 without being contaminated by soiling before use.

The weld spots 5 are, for each of the sections of the article 3, respectively located on the front wall 21 and rear wall 22, as illustrated in FIG. 2.

The attachment force of the article 3 to the walls of the container 2 is weak enough so that the user can, by exerting a pulling force on the article 3, detach it from the container 2. Owing to invention, the user has, after opening of the container 2, an article 3 in the unfolded state, which is itself easier to handle in order to apply it to the zone to be treated.

In the example illustrated, the attachment of the article 3 to the walls of the container 2 is carried out for each section of the article using two weld spots 5 that are for example each located in the vicinity of a corner of the article opposite the fold line 4, as can be seen in FIG. 2.

Of course, the invention is not limited to the attachment illustrated between the article 3 and the container 2, and the attachment between the two can be carried out by spot welds positioned otherwise, or even by one or more weld lines that extend for example over all or part of the width of the article 3.

The attachment between the article 3 and the container 2 may be achieved by local melting of material, owing for example to an inner layer 210 of thermoplastic material present on the front wall 21 and rear wall 22, for example of polyethylene, as illustrated in FIG. 5.

The welding is preferably carried out from the outside of the container 2 by transmitting thermal energy to the weld zone, for example via ultrasounds, or via conduction or convection.

The weld spots 5 may be slightly offset relative to one another when the article 3 is seen from the front in the container 2 before opening, which may be advantageous when the welds are produced simultaneously, in order to reduce the risk of attachment between the two walls 21 and 22, linked for example to a spread of the molten thermoplastic material through the entire thickness of the article 3.

The step of supplying energy via ultrasounds is illustrated in FIG. 4, where sonotrodes 8 have been represented slightly offset with respect to the bottom 9 of the container 2.

Although the attachment of the article 3 to the front or rear walls is preferably carried out owing to the presence of at least one layer 210 of thermoplastic material on the inner faces of the front wall 21 and rear wall 22 as illustrated in FIG. 5, it is also possible, without departing from the scope of the present invention, to produce the welds owing to the presence of at least one thermoplastic material on the article 3 itself. In this case, the article may comprise fibres that locally melt and are attached to the front wall 21 or rear wall 22. As a variant, the article locally comprises a hot-melt material which has been added to the fibrous substrate and which melts when energy is supplied from the outside of the container 2, in order to enable attachment of the article 3 to the front wall 21 and rear wall 22 of the container. As a further variant, both the article 3 and the front wall 21 and rear wall 22 comprise at least one hot-melt material that melts when energy is supplied in order to produce the welds 5.

The invention is not limited to a device having, when seen from the front, a rectangular contour, such as illustrated in FIG. 1.

In particular it is possible to give the container 2 any shape suitable for the nature and shape of the article 3 contained inside. For example, it is possible to produce the device 1 with a container 2 of semicircular shape, as illustrated in FIG. 6A, with for example one or more gripping tabs 23 in the continuation of the front wall 21 and rear wall 22, opposite the bottom 9 of the container 2.

It is also possible, as illustrated in FIG. 6B, to give the packaging device 1 a contour shape that is polygonal when seen from the front, for example trapezoidal. Also illustrated in this FIG. 6B is the possibility of folding up the article 3 in a dissymetrical manner, for example in the form of two sections 31 and 32 that are unequal with respect to the fold line 4 and which do not superpose exactly.

In FIG. 6B, the sections 31 and 32 are attached to the front and rear walls by weld lines 5. The weld may also be peripheral about the article contained, where appropriate.

The article 3 may be positioned inside the container 2 by being folded up on itself along more than one fold line. By way of example, illustrated in FIGS. 7 to 9 is a device in which the article 3 comprises several fold lines 4, being for example accordion-folded on itself.

The container 2 may for example be in the form of a tray comprising a hollow body that constitutes the rear wall 22. The latter is sealed by a cover in the upper part, which constitutes the front wall 21. The hollow body may be thermoformed.

One of the end sections 31 of the article 3 is attached by welding to the cover 21 whilst the other end section 32 is attached by welding to the body 22 of the container 2, especially to the bottom thereof.

Thus, when the user separates the cover 21 from the body 22, the end sections 31, 32 remain attached respectively to the cover 21 and to the body 22, which makes it possible to open out the article 3 without having to grasp it directly. Next, the user can detach, by pulling, each end section 31, 32 from the corresponding wall of the container 2 and use the article 3.

FIGS. 10 and 11 are two block diagrams illustrating two variants of manufacturing processes.

In the example from FIG. 10, the welding of the article to the container takes place before the impregnation of the article with the product and the closure of the container.

In the variant from FIG. 11, the article is impregnated before the closure of the container and the welding takes place once the container is sealed, with, on the inside, the article impregnated by the product.

Illustrated in FIGS. 13A to 13F is a variant of the device 1 according to the invention, in which the article 3 is in the form of a mask folded up on itself about a fold line 4.

The article 3 comprises cut-outs 131 for the eyes, nose and mouth, as illustrated.

Two weld spots 5 ensure the attachment of each of the sections of the article to the front wall 21 and rear wall 22 of the container 2, respectively.

Figure 13A:
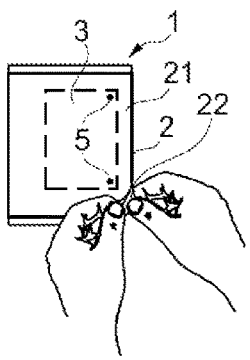
Figure 13B:
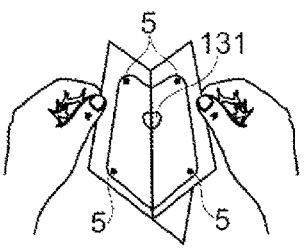
Figure 13C:
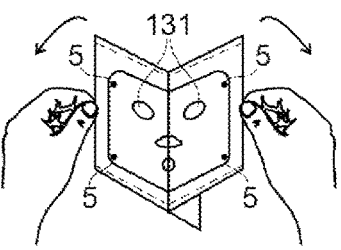
Figure 13D:
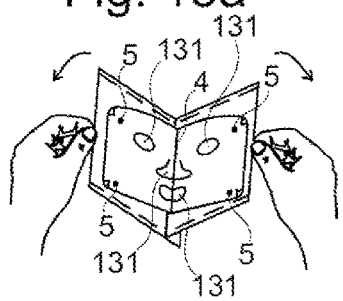

In order to use the article, the user begins by grasping, after having cut, where appropriate, one side, the front wall 21 and rear wall 22 and separates them. During this separation, the two sections of the mask remain respectively attached to the front wall 21 and rear wall 22, as can be seen in FIGS. 13B to 13D.

Figure 13E:
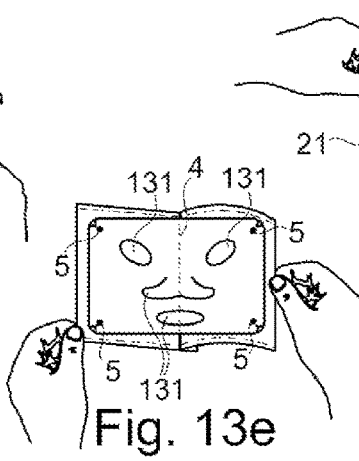
Figure 13F:
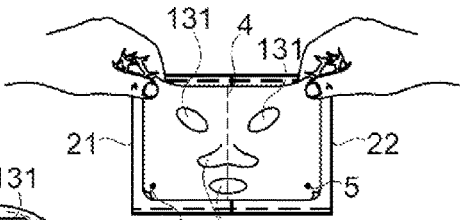

Once the container 2 is completely open, or practically open, the mask is opened out, as illustrated in FIG. 13E. The user can then grasp it and, by exerting a slight pulling force in order to break the weld spots 5, detach it from the container 2 in order to use it.

Preferably, the article remains attached via the welds to the front and rear walls of the container when the latter is open; as a variant, the article is attached to the container so that the article is unfolded before the container is completely open, the remainder of the opening of the container causing the breakage of at least some of the welds of the article with the front or rear walls.

Needless to say, the invention is not limited to the examples that have just been described.

In particular, the invention finds application in fields other than that of cosmetics and the packaging device is, for example, used for packaging a household cleaning wipe, which may be fastened, where appropriate, to a broom or any other suitable support.

The container 2 may also be produced in the form of a case comprising two parts, for example rigid parts, which can pivot relative to one another owing to a hinge, the article being attached respectively to each of the parts by welding.

The expression "comprising a" is synonymous with "comprising at least one", unless specified to the contrary.

The invention claimed is:

1. Device for packaging a product, comprising:
a container having joined front and rear walls,
an article in the form of a mask packaged in a folded state inside the container, this article bearing said product and having one or more cut-outs for eyes, nose and/or mouth, the article having at least two sections separated by at least one fold line, the at least two sections being respectively attached to the front and rear walls by weld zones, so that on opening the container the separation of the front and rear walls automatically leads to the unfolding of the article at least about said at least one fold line, the article being configured to be separated from the walls via a pulling force exerted on the weld zones during use of the article,
a surface area of the weld zones by which the article is attached by welding to respective opposite walls of the container being less than or equal to 1 cm$^2$ per section of the article.

2. Device according to claim 1, the article having been attached to the wall or walls of the container by welding performed from the outside of the container.

3. Device according to claim 1, there being only one fold line, the at least two sections being of symmetrical shape or not symmetrical with respect to the fold line.

4. Device according to claim 1, the article comprising a sheet of a nonwoven material.

5. Device according to claim 1, the product being in the form of a fluid composition, the article being impregnated with said product.

6. Device according to claim 1, the article comprising a hot-melt material.

7. Device according to claim 1, the front and rear walls of the container having, on their inner face, a layer of a hot-melt material.

8. Device according to claim 1, wherein the at least one fold line of the article being located at an edge of the container opposite to the edge where the opening begins.

9. Device according to claim 1, the weld zone(s) being anchorage points.

10. Device according to claim 9, comprising two anchorage points on each wall of the container.

11. Device according to claim 10, the anchorage points being located close to corners or free ends of each section of the article.

12. Device according to claim 6, the article comprising fibers of a hot-melt material.

13. Device according to claim 1, wherein the surface area of the weld zones by which the article is attached by welding to respective opposite walls of the container being between 0.1 mm$^2$ and 10 mm$^2$ per section of the article.

\* \* \* \* \*